United States Patent [19]

Beck et al.

[11] Patent Number: 5,411,034
[45] Date of Patent: May 2, 1995

[54] AIR SENSITIVE RUPTURE INDICATING CONDOM

[76] Inventors: R. Bruce Beck; M. Angela Beck, both of 124 Huntzinger Rd., P.O. Box 151, Wernersville, Pa. 19565

[21] Appl. No.: 289,392
[22] Filed: Aug. 12, 1994
[51] Int. Cl.6 .................................................. A61F 6/04
[52] U.S. Cl. ..................................... 128/844; 128/918
[58] Field of Search ................ 128/842, 844, 918; 604/347–353

[56] References Cited

U.S. PATENT DOCUMENTS

| 5,010,871 | 4/1991 | Christina | 128/842 |
|---|---|---|---|
| 5,024,852 | 6/1991 | Besnel | 128/844 |
| 5,045,341 | 9/1991 | Shlenker | 128/844 |
| 5,137,032 | 8/1992 | Harmon | 604/349 |
| 5,284,158 | 2/1994 | Mallette | 128/844 |
| 5,284,159 | 2/1994 | Wilk | 128/842 |
| 5,317,760 | 6/1994 | Best | 128/844 |

*Primary Examiner*—Michael A. Brown
*Attorney, Agent, or Firm*—Lowe, Price, LeBlanc & Becker

[57] ABSTRACT

A condom including three layers, first and third layers which are of elastomeric material with a second layer sandwiched between the first and third layers including a colorless, air sensitive material. When the colorless, air sensitive material is exposed to air because of a rupture in said first or third layers of said condom, the colorless, air sensitive material changes color to alert the user that the integrity of the condom is compromised.

7 Claims, 1 Drawing Sheet

AIR SENSITIVE RUPTURE INDICATING CONDOM

TECHNICAL FIELD

The present invention relates to a condom device, having a color indicator. The condom incorporates a visual alert to a rupture or hole in the condom. This is accomplished by providing two layers of material with a sandwiched, colorless agent there between. In the event the colorless agent is exposed to air because of a rupture, it changes color to alert the user that the integrity of the condom is compromised.

BACKGROUND

U.S. Pat. Nos. 4,843,014 and 4,910,803 to Cukier disclose bodily fluid protection apparel, such as a condom, that are constructed to alert a wearer that a breach in the apparel has occurred. This is accomplished by providing a first layer impervious to bodily fluid and a second layer supporting the first layer, the second layer comprising a bodily fluid detection means indicating the presence of bodily fluid.

U.S. Pat. No. 5,224,221 to Richardson et al. discloses tamper or damage indicating members. The members, which are typically in the form of a bi-layer glove, comprise an inner layer and an outer layer, both being liquid- and air-impermeable. The outer layer is sealed to the inner layer so as to surround a zone of the inner layer which is not sealed to the outer layer. The space between the layers in the above-mentioned zone is free of air, and the outer layer is translucent or transparent in the area overlying that zone and having a contrasting color relative to the color of the inner layer, so as to provide a visual indication (a change in the perceived color) when the outer layer is breached, as a result of tampering, accidental damage or the like.

U.S. Pat. Nos. 87,932; 3,759,254; 4,807,611; 4,808,174; 4,898,184; 4,981,147; 5,070,890; 5,156,165 disclose alternative forms of condoms and are incorporated by reference herein in their entireties.

None of the patents discloses the concept of providing a condom having a colorless agent between two layers of material which will change color when exposed to air and/or bodily fluid to alert the user to a rupture.

There is a major problem with condoms. The problem is that the wearer of the condom cannot easily determine whether the condom has been breached, ruptured or otherwise circumvented unless such a breach or circumvention is noticeable to the wearer. This problem is particularly acute in the case of AIDS, other viral diseases such as hepatitis, and certain bacterial infections owing to the extraordinarily small size, even by microscopic standards, of the microbial etiologic agents of these diseases. There are literally billions of these disease-causing agents in even a microscopic droplet of blood or other bodily fluid. Consequently, an individual, even though wearing a protective condom, may unwittingly be exposed to an infectious agent such as the AIDS virus because the wearer cannot detect the fact that he is in contact with a microscopic amount of bodily fluid or blood.

The condom according to the present invention, solves many of the prior art problems by providing for a condom which incorporates a visual alert to a rupture or hole in the condom. This is accomplished by providing two layers of material with a second sandwiched layer with an air sensitive, colorless agent there between first and third layers. In the event the colorless agent is exposed to air because of a rupture, it changes color to alert the user that the integrity of the condom is compromised.

DISCLOSURE OF THE INVENTION

The present invention provides for a condom comprising three layers, first and third layers which are of elastomeric material with a second layer sandwiched between the first and third layers including a colorless, air sensitive material such as a chemical or dye, wherein when the colorless, air sensitive material is exposed to air because of a rupture in said first or third layers of said condom, the colorless, air sensitive material changes color to alert the user that the integrity of the condom is compromised.

In a preferred embodiment the colorless, air sensitive material is selected from the group consisting of leucocrystal violet and leuco-malachite green.

In an alternative embodiment the second layer may also include a bodily fluid detection means. Any one of a number of bodily fluids, including blood, saliva, and semen, can be detected by the detection means.

In this embodiment the bodily fluid detecting means may be selected from the group consisting of Benedicts solution, Haynes solution, and Barfoeds solution, peroxidase, pseudoperoxidase, guaiac acid, benzidene, ortho-tolidine, ortho-dianisidine, cumene hydroperoxide and tetramethylbenzedene.

DESCRIPTION OF THE INVENTION

Figure 1:
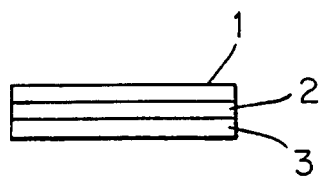
FIG. 1 shows a schematic of the three layers of the condom of the invention. Layers (1) and (3) comprise one or more elastomeric materials. Layer (2) comprises a colorless, air sensitive material.
Figure 2:
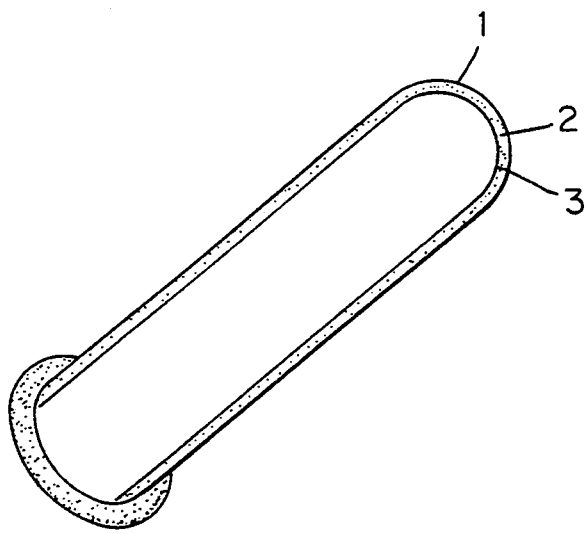
FIG. 2 is a schematic of an embodiment of the air sensitive, rupture indicating condom of the present invention. Layers (1) and (3) comprise one or more elastomeric materials. Layer (2) comprises a colorless, air sensitive material.

The condom of the invention is designed for any wearer who may come in contact with the bodily fluids of a person suspected of harboring a contagious malady or who seeks protection by means of a barrier from bodily fluids. The protective condom alerts the wearer to the fact that a rupture in the condom has occurred which may allow the passage of bodily fluid, possibly containing the infectious agent from which a wearer is seeking protection. The wearer is alerted to this danger by incorporating between two layers of the condom, a colorless, air sensitive material which is a detection means that changes color and alerts the wearer that a rupture has occurred in the condom which may allow bodily fluid to penetrate the condom.

The invention provides for the detection of a rupture which may allow for the passage of bodily fluid therethrough, or in another way circumvented, a first, impervious, boundary layer of protective condom. Detection is accomplished by providing for a second layer, which is positioned in between the first and third layers. The second layer includes a colorless, air sensitive which can indicate rupture of the inner, third or outer, first layer.

Activation of the air sensitive material or agent is initiated by the presence of air which triggers a colorless marker chemical specific for air to change or adopt a color (change from colorless to a color) upon contact with air to alert the wearer of rupture.

The central or second layer thus includes a colorless, air sensitive material and may optionally also include a bodily fluid sensitive material. The air sensitive material can be a chemical or dye which reacts quickly with the air to cause a sudden change in color. Examples of air sensitive materials according to the present invention are leuco-crystal violet and leuco-malachite green. Both of these dyes are colorless until exposed to air. Upon exposure to air they change to violet and deep green, respectively.

If leuco-crystal violet and leuco-malachite green are used they must be inserted between the first and third latex layers, or other suitable material, of the condom in an oxygen free environment, such as a chamber of carbon dioxide or nitrogen. Thus a conventional molding process would take place in an oxygen free environment. The second, colorless dye layer may preferably be spray coated onto the first or third layer and finally, the first or third layer of molded latex or other suitable material as known in the art would be sealed to the other layers at the base of the condom, to insure airtight integrity.

Optionally, a bodily fluid detection means may also be incorporated in the second layer. The air sensitive material detection means used in the second layer of the invention can be adapted to detect any bodily fluid, especially bodily fluids known to transmit or harbor infectious agents. Such bodily fluids include blood, saliva, mucous, and semen. Dyes permitting colorimetric detection, such as for blood, are known in the art. The specific formulations of these compositions vary depending on the fluid to be detected. If more than one bodily fluid is to be detected-for instance, blood and saliva, then the composition contains formulations for detection of more than one bodily fluid.

It will be appreciated that this invention may be adapted to various kinds of condom depending on both the bodily fluid from which the wearer is seeking protection and the likely mode by which infection is spread. If, protection is being sought from blood, then a condom incorporating the three layers of this invention would be appropriate.

The invention can further be used to provide detection of the movement of bodily fluids even when protection from disease is not sought. In one mode, the instant invention can be adapted to be implemented as a birth control device. In one embodiment, if there is a breach in the condom, a detection means alerts the user of the condom and/or the user's sexual partner that a breach in the condom has occurred. With knowledge of such a breach, an individual could take preventive measures that may lessen the chance of pregnancy in view of the breached condom, such as use of a douche. In an alternative embodiment the condom of the invention is suitable for prevention of sexually transmitted diseases during oral sex. Another advantage that accompanies use of a condom incorporating the instant invention is if the condom user is known to carry a venereal disease or AIDS. In this situation, the sexual partner of the condom wearer can take steps to lessen the chance of infection from the disease as a result of contact with the infectious agent contained in the semen of the condom wearer. In this embodiment an enzyme or other chemical marker, such as hyaluronidase or other chemical principally associated with semen, activates an indicator in the detection means. The presence of semen (and presumptively sperm) can also be achieved using the monosaccharide fructose as a marker chemical. The use of fructose exploits the fact that the presence of fructose is known to be an indicator of the presence of sperm. The mechanism by which this is incorporated into the detection means capitalizes on fructose being a reducing sugar, i.e. a sugar readily oxidized by an alkaline cupric solution. Among the cupric solutions usable for oxidizing reducing sugars are Benedicts, Haynes, and Barfoeds. For example, a Benedicts solution is applied to the material or condom of this invention during manufacture. If, while the item is in use, a breach permits semen to come into contact with the fructose comprising detection means, it would react with the Benedicts solution in a colorimetric manner resulting in a visually detectable color change. As aforementioned, the instant invention is adaptable to detect a variety of bodily fluids. In the case of alerting a wearer to exposure to a bodily fluid possibly containing an infectious agent, the bodily fluid of greatest concern is blood.

If the wearer were seeking protection from blood, the detection means would incorporate chemicals sensitive to blood components, such as, for instance, heme. Compositions for the detection of blood are well known. For instance, most tests for blood in biological specimens exploit the peroxidase or pseudoperoxidase activity of heme derivatives by oxidizing organic compounds used as indicators. The peroxidase substances release, under acidic conditions, hydrogen peroxide or other active oxidants. Acidic components, suitable oxidizable compounds that can form dyes, and typical peroxidic substances are known in the art. Indicator substances oxidizable by the released oxidant then form highly colored reaction products. One indicator reagent that works well is guaiac acid, which, in combination with a developer acting as a reagent to facilitate color formation, forms a color in the presence of blood. Other acceptable reagents include benzidene, ortho-tolidine, ortho-dianisidine, and organic oxides including cumene hydroperoxide and tetramethylbenzedene.

Detection of bodily fluid by this invention is accomplished by a specific bodily fluid coming into contact with an indicator for marker chemical for the specific bodily fluid for which detection is sought. This chemical marker is capable of alerting the wearer of real or potential exposure to bodily fluid. Once alerted, the wearer can quickly change the condom. Desirably, before replacing the compromised condom, the wearer will take steps to assure that his or her exposure to the infectious agent is minimized. Such steps could include, as discussed, washing the exposed area with soap and hot water.

The condom of the present invention may be of the male or female style, as is known in the art. Optionally, the condom may also include germicides, viricides, contraceptives, lubricants, disinfectants or other materials known in the art. The condom may be of the conventional male or female dimensions as is well known in the art.

In one embodiment the condom is made of latex or other suitable material, for example, plastics, copolymers, polyethylene, polypropylene, polyvinylchloride or vinyl.

Use of this invention in its embodiment as a protection against the spread of infectious disease is deemed extremely significant. Many infectious diseases, including AIDS, are not so highly contagious that a momentary or brief exposure to the infectious agent of the disease results in clinical infection. There is usually a relation between the length of time an individual is exposed to an infectious agent and the probability with which the individual will become infected by the infectious agent. Therefore, if an individual is warned promptly that an exposure to an infectious agent has occurred, the individual can promptly take measures to minimize the length of time he is exposed to the infectious agent. By virtue of the detection means, a wearer of the protective, air sensitive condom of this invention will be quickly warned that he has been exposed to an infectious agent. This being the case, the wearer can quickly remove the protective condom and take steps to cleanse himself of the infectious agent. For many diseases, the cleansing steps can be quite simple including merely washing the area exposed to an infectious agent with soap and hot water.

In sum, the condom of the present invention is a material adaptable to form a bodily fluid protection device that can alert a wearer that a breach in the condom has occurred. The condom incorporates a visual alert to a rupture or hole in the condom. This is accomplished by providing first and third layers of elastomeric material with a second layer sandwiched between the first and third layers which comprises an air sensitive colorless agent. In the event the colorless agent is exposed to air because of a rupture, it changes color to alert the user that the integrity of the condom is compromised.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

We claim:

1. A condom comprising three layers, first and third layers which are of elastomeric material with a second layer sandwiched between the first and third layers including a colorless, air sensitive material, wherein when said colorless, air sensitive material is exposed to air because of a rupture in said first or third layers of said condom, said colorless, air sensitive material changes color to alert the user that the integrity of the condom is compromised.

2. A condom as in claim 1, wherein said colorless, air sensitive material is selected from the group consisting of leuco-crystal violet and leuco-malachite green.

3. A condom as in claim 1, wherein said second layer further comprises a bodily fluid detecting means.

4. A condom as in claim 3, wherein said bodily fluid detecting means is selected from the group consisting of Benedicts solution, Haynes solution, and Barfoeds solution, peroxidase, pseudoperoxidase, guaiac acid, benzidene, ortho-tolidine, ortho-dianisidine, cumene hydroperoxide and tetramethylbenzedene.

5. A condom as in claim 3 wherein said condom further comprises an agent selected from the group consisting of germicides, viricides, contraceptives, lubricants, and disinfectants.

6. A condom as in claim 1 wherein said condom is a male or female condom.

7. A condom as in claim 1 wherein said first and third layers comprise an elastomeric material selected from the group consisting of latex, plastics, copolymers, polyethylene, polypropylene, polyvinylchloride and vinyl.

* * * * *